(12) United States Patent
Her

(10) Patent No.: US 11,129,967 B2
(45) Date of Patent: Sep. 28, 2021

(54) MEDICAL TUBE HOLDER

(71) Applicant: SMHERS, Paju-si (KR)

(72) Inventor: Se Hee Her, Seoul (KR)

(73) Assignee: SMHERS, Paju-si (KR)

( * ) Notice: Subject to any disclaimer, the term of this patent is extended or adjusted under 35 U.S.C. 154(b) by 354 days.

(21) Appl. No.: 16/303,152

(22) PCT Filed: May 19, 2017

(86) PCT No.: PCT/KR2017/005256
§ 371 (c)(1),
(2) Date: Dec. 18, 2018

(87) PCT Pub. No.: WO2017/200356
PCT Pub. Date: Nov. 23, 2017

(65) Prior Publication Data
US 2019/0262583 A1    Aug. 29, 2019

(30) Foreign Application Priority Data
May 20, 2016    (KR) .................. 10-2016-0062135

(51) Int. Cl.
A61M 25/02    (2006.01)
B65D 33/06    (2006.01)
(Continued)

(52) U.S. Cl.
CPC ............. *A61M 25/02* (2013.01); *A61M 31/00* (2013.01); *A61M 2025/0293* (2013.01); *A61M 2025/0681* (2013.01)

(58) Field of Classification Search
CPC .................. A61M 25/02; A61M 31/00
(Continued)

(56) References Cited

U.S. PATENT DOCUMENTS 4,112,541 A * 9/1978 Tetradis ................ A45F 5/1026
24/30.5 R
4,871,358 A * 10/1989 Gold .................. A61M 25/0119
604/271
(Continued)

FOREIGN PATENT DOCUMENTS

EP    2636421 A1    9/2013
KR    10-0451020 B1    10/2004
(Continued)

OTHER PUBLICATIONS

International Search Report for PCT/KR2017/005256 dated Aug. 18, 2017 from Korean Intellectual Property Office.
(Continued)

Primary Examiner — Paul T Chin
(74) Attorney, Agent, or Firm — Revolution IP, PLLC

(57) ABSTRACT

A medical tube holder includes: a holder body having a through hole therein through which a medical tube is passed; and an elastically deformable protruding member provided in the holder body in a direction of narrowing a width of the through hole to increase a frictional force with an outer circumferential surface of the medical tube, wherein the elastically deformable protruding member is brought into close contact with the outer circumferential surface of the medical tube passed through the through hole, such that the holder body is fitted over the medical tube.

12 Claims, 8 Drawing Sheets

(51) Int. Cl.
*A61M 31/00* (2006.01)
*A61M 25/06* (2006.01)

(58) Field of Classification Search
USPC .................................. 294/219, 137, 171
See application file for complete search history.

(56) References Cited

U.S. PATENT DOCUMENTS

| | | | | |
|---|---|---|---|---|
| 5,217,439 | A | | 6/1993 | McClusky |
| 5,242,428 | A | * | 9/1993 | Palestrant ............. A61M 25/01 604/265 |
| 5,730,231 | A | * | 3/1998 | Racodon ................ B25D 3/00 16/431 |
| 5,860,190 | A | * | 1/1999 | Cano ..................... A47G 21/02 16/422 |
| 6,142,977 | A | | 11/2000 | Kolberg et al. |
| 6,578,709 | B1 | | 6/2003 | Kavanagh et al. |
| 6,719,342 | B2 | * | 4/2004 | Shinmoto ............. A45F 5/1046 294/137 |
| D903,111 | S | * | 11/2020 | Pupino ..................... D24/130 |
| 10,875,682 | B1 | * | 12/2020 | Laudon ................. B65D 25/32 |
| 2006/0264979 | A1 | * | 11/2006 | Shepard ................ A61M 25/02 606/151 |
| 2009/0247827 | A1 | * | 10/2009 | Secrest ................ A61B 1/0014 600/131 |
| 2012/0037771 | A1 | * | 2/2012 | Kitchen ................ G06F 1/1632 248/223.41 |
| 2012/0239005 | A1 | * | 9/2012 | Conway ............ A61M 25/0097 604/544 |
| 2014/0237798 | A1 | | 8/2014 | Cude |
| 2014/0262859 | A1 | | 9/2014 | Knapp et al. |
| 2016/0256663 | A1 | * | 9/2016 | Rajagopalan ......... A61F 5/0013 |

FOREIGN PATENT DOCUMENTS

| | | |
|---|---|---|
| KR | 10-0484458 B1 | 4/2005 |
| KR | 10-2008-0084387 A | 9/2008 |
| KR | 10-2015-0128902 A | 11/2015 |
| WO | 2011/129780 A1 | 10/2011 |
| WO | 2015/105942 A1 | 7/2015 |
| WO | 2015/142506 A1 | 9/2015 |

OTHER PUBLICATIONS

Extended European search report of EP17799713 dated Dec. 16, 2019.

* cited by examiner

MEDICAL TUBE HOLDER

TECHNICAL FIELD

The present invention relates generally to a tube holder. More particularly, the present invention relates to a tube holder, which is configured to surround the an outer circumferential surface of a medical tube such as a catheter that is inserted into a human body, so that a user can insert the medical tube into the human body or remove the same from the human body without directly touching the medical tube.

BACKGROUND ART

A catheter is a kind of tube used for medical use, and is widely referred to as a general tubular device. Catheters can be of various materials, sizes, and shapes depending on their use, and are used for discharge of the body fluid in a body cavity or various organs, suction of the perfusion fluid for cleaning, measurement of the cardiovascular behavior or the central venous pressure, injection of drug or contrast agent, and the like.

The medical tube is usually made of clear synthetic resin, can be freely bent, and is designed to be sufficiently long such that the end portion thereof reaches the desired area. Meanwhile, in order to insert the medical tube into the human body, sterilized gloves must be first put on. Since the tube is inserted into the body, if the hygienic care is not thoroughly performed in inserting the tube, a new disease may be transferred to a patient and the existing disease may be worsened. In particular, in patients with infectious diseases such as AIDS, infections of germs through the tube may result serious consequences.

Despite the importance of hygiene in the insertion of the medical tube, some practitioners touch the tube with non-sterile gloves or bare hands because it is troublesome to put on sterile gloves, which is a necessity, it takes time to prepare gloves, and there is the inconvenience of sweating of the hands.

To solve this problem, in the document of Korean Patent No. 10-0451020, there has been disclosed a holder for a medical tube. By gripping the medical tube through the holder, it is possible to prevent the user from using a sterilizing tweezers or directly gripping the medical tube, so it has a sanitary effect.

However, the conventional tube holder is problematic in that it can be applied only to a medical tube having a predetermined diameter and cannot be applied to medical tubes having different diameters. Therefore, a separate holder must be prepared for use with medical tubes of different specifications.

Meanwhile, in order to smoothly insert the medical tube into the human body, a lubricant jelly for medical use, which is a lubricant, is usually applied to the outer circumferential surface of the medical tube, but applying the lubricant in this way requires additional work, which reduces ease of use.

DISCLOSURE

Technical Problem

Accordingly, the present invention has been made keeping in mind the above problems occurring in the prior art, and an object of the present invention is to provide a tube holder, which is applied to medical tubes of various thicknesses.

Another object of the present invention is to provide a tube holder, in which lubricant is applied to an outer surface of a medical tube using the tube holder.

Technical Solution

In order to accomplish the above object, according to one aspect of the present invention, there is provided a tube holder including: a holder body having a through hole therein through which a medical tube is passed; an elastically deformable protruding member protruding from an inner circumferential surface of the through hole of the holder body in direction of narrowing the through hole; and lubricant stored in a storage space of the protruding member or between the protruding members, wherein the lubricant is applied to the outer circumferential surface of the medical tube disposed in the through hole of the holder body.

The protruding member may be a plurality of protrusions having storage spaces therein and protruding from the inner circumferential surface of the through hole of the holder body, and the lubricant may be stored in the protrusions or between two neighboring protrusions.

The protrusions may be configured such that heights thereof are increased or decreased in a direction from an inlet of the through hole toward a center thereof.

The protrusions may be made of flexible material to be bent in a direction of being brought into contact with the outer circumferential surface of the medical tube in a process of inserting the medical tube into the through hole, and the protrusions may be broken by a force to insert the medical tube or an external force to press the protrusions, such that the lubricant stored in the storage spaces is discharged outside.

The protruding member may be constituted by the plurality of protrusions, and the lubricant may be stored in storage spaces of a part of the plurality of protrusions.

The protruding member may be an inner blanket covering the inner circumferential surface of the holder body, the inner blanket may be made of flexible material, and lubricant may be stored in a space between the inner circumferential surface of the holder body and the inner blanket and then be applied to the outer circumferential surface of the medical tube inserted into the through hole.

The protruding member may be a storage capsule inserted into the inner circumferential surface of a storage space of the holder body, lubricant may be stored in the storage capsule, and the storage capsule may be broken by an external force and the lubricant stored therein may be discharged.

The storage capsule may be inserted into an enlarged portion at an inlet enlarged in a direction of widening a diameter of the through hole of the holder body.

The holder body may be configured such that a planar base material with opposite ends separated from each other is rolled in a cylindrical shape having the through hole therein.

The holder body may be covered with an inner blanket on an inner surface thereof, and the inner blanket may be provided with a plurality of pockets in which the lubricant is stored.

Advantageous Effects

The tube holder according to the present invention configured as described above has the following advantageous effects.

Since the inner surface of the tube holder of the present invention is provided with the protruding member and the protruding member is elastically deformable, in the process of inserting the medical tube, the protruding member is deformed to be brought into close contact with the outer surface of the medical tube. Thus, one holder can be applied to medical tubes having various thicknesses, so the compatibility of the holder is improved.

Further, the lubricant is stored in the tube holder of the present invention, and the stored lubricant may be applied to the outer circumferential surface of the medical tube. Thus, the user can easily apply the lubricant using the tube holder, and additional work for applying the lubricant is not required, which improves ease of operation.

In particular, when the protruding member of the present invention is constituted by protrusions, the protrusions can serve to evenly apply the lubricant to the outer circumferential surface of the medical tube, whereby it is possible to efficiently apply the lubricant to the outer surface of the medical tube by using the tube holder.

MODE FOR INVENTION

Figure 1:
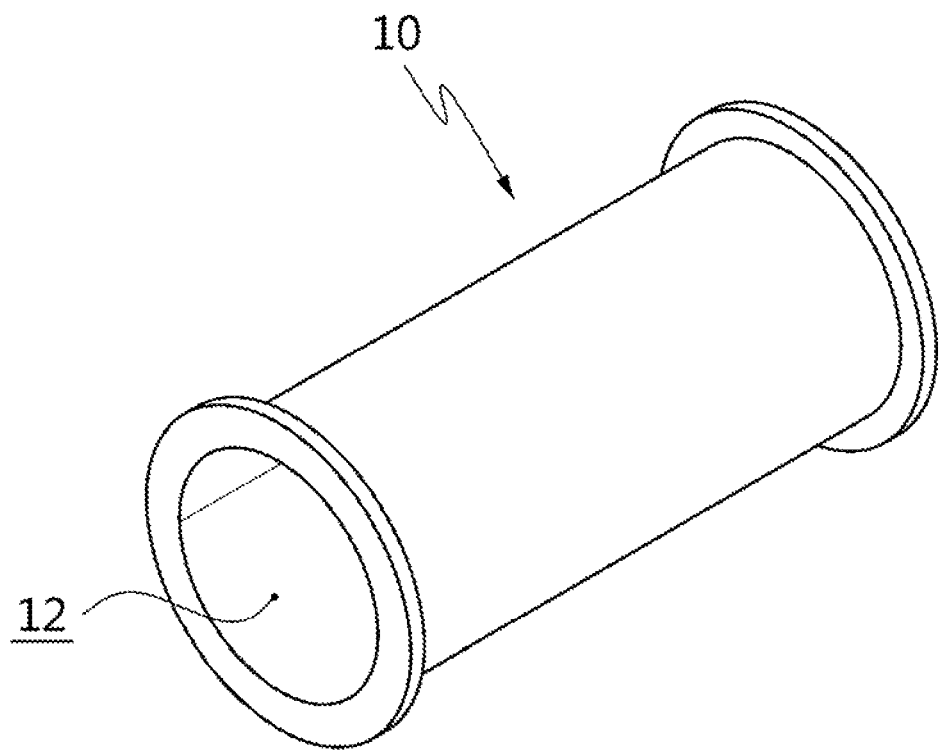
FIG. 1 is a perspective view showing a structure of an embodiment of a tube holder according to the present invention.
Figure 2:
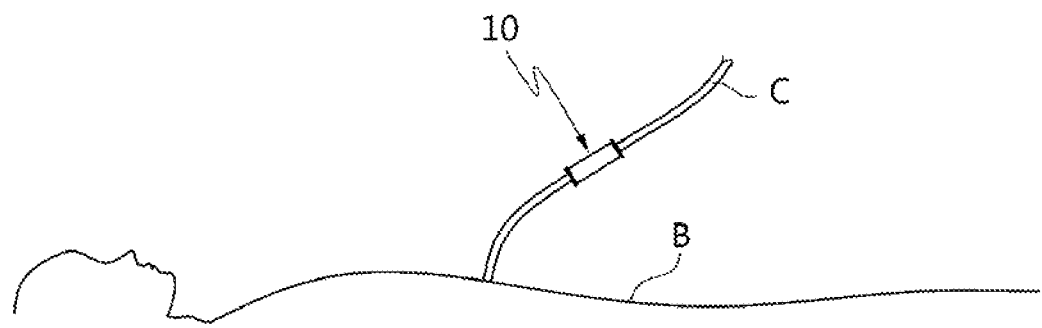
FIG. 2 is an exemplary view showing a state of use of the present invention by applying the same to a medical tube.

Reference will now be made in greater detail to an exemplary embodiment of the present invention, an example of which is illustrated in the accompanying drawings. Wherever possible, the same reference numerals will be used throughout the drawings and the description to refer to the same or like parts. Further, in the following description of the invention, if the related known functions or specific instructions on configuring the gist of the present invention unnecessarily obscure the gist of the invention, the detailed description thereof will be omitted.

Further, it will be understood that, although the terms first, second, A, B, (a), (b), etc. may be used herein to describe various elements, these elements should not be limited by these terms. These terms are only used to distinguish one element, from another element. It will be understood that when an element is referred to as being "coupled" or "connected" to another element, it can be directly coupled or connected to the other element or intervening elements may be present therebetween. In contrast, it should be understood that when an element is referred to as being "directly coupled" or "directly connected" to another element, there are no intervening elements present.

A medical tube holder 10 (hereinafter, referred to as 'tube holder') according to the embodiment is a cylindrical member having a predetermined diameter and length configured to allow a medical tube C to pass therethrough so as to envelop an outer circumferential surface of the tube. This is based on the view that a user is able to hold the medical tube C through the holder so that the tube can be inserted without direct contact with the hand.

In addition, the tube holder 10 of the embodiment is not limited to use in medical tube C, but can also be used for insertion of a known guide wire which is inserted before the tube is inserted.

FIG. 1 is a perspective view showing an appearance of the tube holder 10 according to an embodiment of the present invention. As shown in the drawing, the tube holder 10 of the embodiment is in a cylindrical shape with opposite ends being open, and has a through hole 11 at the center thereof through which the medical tube C can be passed.

Figure 5:
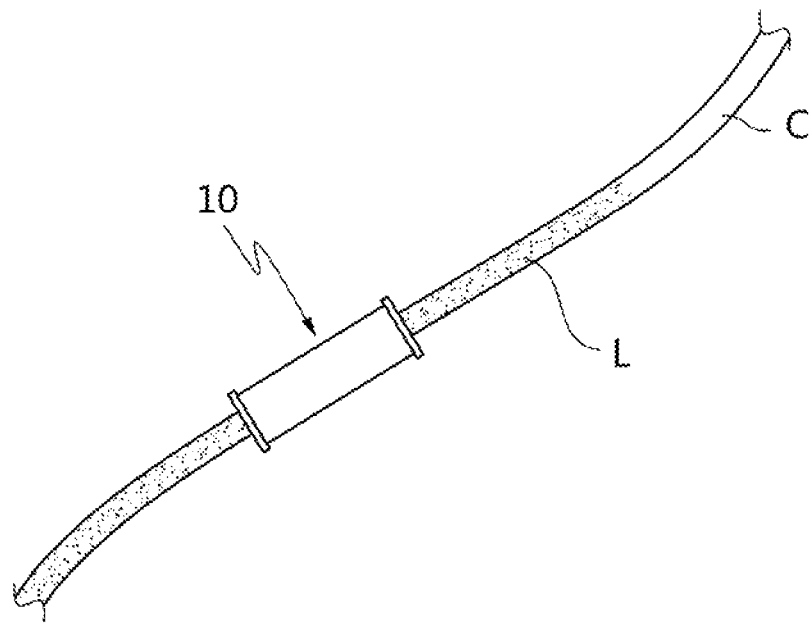
FIG. 5 is a view showing a state where lubricant is applied to an outer circumferential surface of the medical tube by using the tube holder of the present invention.

The tube holder 10 has an elastic restoring force, such that it is compressed when the outer circumferential surface thereof is pressed by hand and is restored to the original state thereof when the pressing force is removed. In other words, as shown in FIG. 5, when a force is externally applied in the direction of the arrow P, the holder is pushed inward to press and pinch the outer circumferential surface of the medical tube C inserted therein, and when the applied force is removed, the original cylindrical shape is restored.

The tube holder 10 may be made of an elastic material selected from the group consisting of silicone, natural rubber, SBR rubber (styrene-butadiene rubber), NBR rubber (acrylonitrile-butadiene rubber), polyethylene resin, EVA resin (ethylene-vinyl acetate resin), PVC resin, and sponge. Of course, the material of the tube holder 10 is not necessarily limited thereto, and may be made of any material that has an elastic restoring force or has a property of maintaining a state of containing lubricant in the form of a jelly due to a moisturizing property so as to provide a frictional force against the outer circumferential surface of the medical tube C in the compressed state.

In order for the user to easily grip the medical tube C without directly touching the medical tube C, it is preferable that the tube holder 10 has a sufficiently long body.

Meanwhile, the inner diameter of the through hole 11 of the tube holder 10 is larger than the outer diameter of the medical tube C. However, as will be described below, the tube holder 10 is provided with a protruding member 20 on the inner circumferential surface thereof, such that the protruding member 20 is rubbed against the outer surface of the medical tube C to prevent the tube holder 10 from being away from the medical tube and excessively moved undesirably.

The tube holder 10 is configured such that a cylindrical holder body forms a frame thereof, and the inner circumferential surface of the through hole 11 of the holder body is provided with a contact means in a direction of narrowing a width of the through hole 11 of the holder body. The contact means is a part to increase a frictional force against the outer circumferential surface of the medical tube, and may be constituted by a following protruding member 20 or may be a part varying the width of the through hole 11.

Of the contact means, to be specific to the protruding member 20, the protruding member 20 protrudes from the inner circumferential surface of the through hole 11 of the holder body in the direction of narrowing the through hole 11 of the holder body, and is made of elastically deformable material. Thus, in the process of inserting the medical tube C into the through hole 11, the protruding member is elastically deformed by the medical tube C to be rubbed against the outer surface of the medical tube C.

Figure 3:
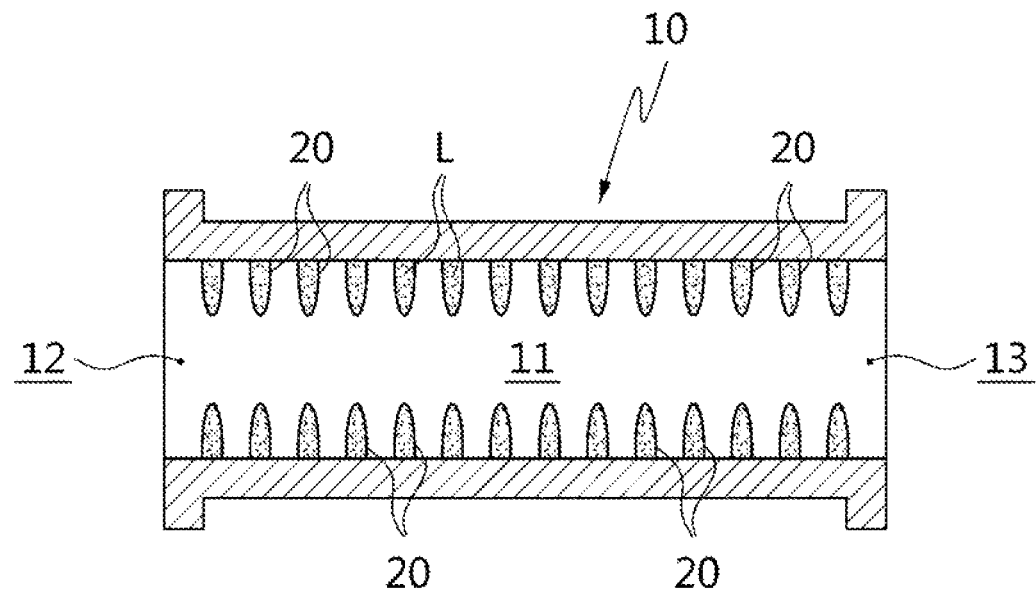
FIG. 3 is a sectional view showing an internal structure of the tube holder according to a first embodiment of the present invention.

FIG. 3 shows a first embodiment of the tube holder 10. As shown in the drawing, the tube holder 10 is formed with the through hole 11 therein, with an inlet 12 and an outlet 13 formed at opposite ends thereof, respectively. The inlet 12 and the outlet 13 are distinguished for convenience, and the inlet and the outlet may be reversed because there is no distinction between front and back of the tube holder 10 of the present invention.

The tube holder 10 is provided with the protruding member 20 therein, wherein the protruding member 20 protrudes in the direction of narrowing the through hole 11. In the embodiment, a plurality of protruding members 20 is arranged at regular intervals along the length direction of the tube holder 10. Further, the protruding member 20 may be configured such that a plurality of protruding members 20 are formed continuously along the inner circumferential surface of the through hole 11 of the tube holder 10 or may be a long extended rib. In the embodiment, the protruding member 20 is in the form of protrusion, and two protruding members are provided along the inner circumferential surface of the through hole 11. In FIG. 3, the protruding member is provided respectively at the upper and lower portion of the through hole 11.

In the protruding member 20, lubricant L is stored. The lubricant L is applied to the outer circumferential surface of the medical tube C, so that the medical tube C can be easily inserted into a human body B. The lubricant L is stored in the storage spaces inside the protruding member 20, is discharged from the storage spaces when the medical tube C is rubbed against the protruding member 20 to break the protruding member 20 or the user presses the tube holder 10 to break the protruding member 20, and then is applied to the outer circumferential surface of the medical tube C.

Figure 4:
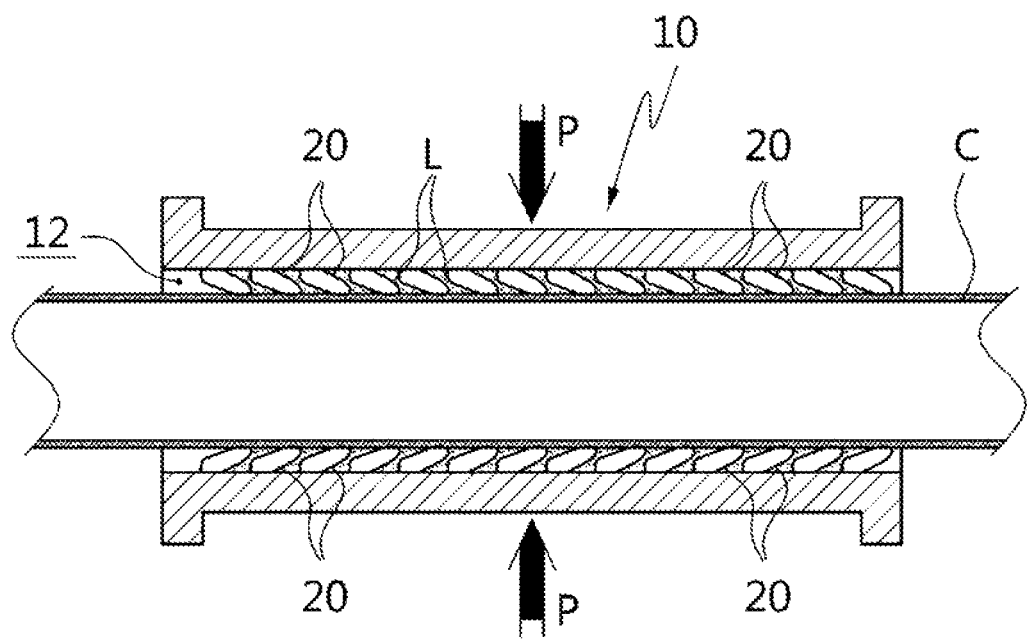
FIG. 4 is a sectional view showing a state where a medical tube is inserted into the tube holder of the present invention.

The protruding member 20 has a protruding structure with a predetermined thickness and is made of a thin membrane having a storage space therein. Thus, when the membrane constituting the protruding member 20 is broken or torn, the lubricant L stored in the storage space is discharged outside and is applied to the outer circumferential surface of the medical tube C. In FIG. 4, it is shown that the protruding member 20 is elastically deformed since the medical tube C is inserted into the through hole 11 of the tube holder 10.

In particular, the protruding member 20 serves as a kind of brush made of an elastic material, to more evenly apply the lubricant L onto the outer circumferential surface of the medical tube C. In other words, when the tube holder 10 is moved along the medical tube C after the lubricant L is discharged from the protruding member 20, the protruding member 20 serves as a brush to evenly apply the lubricant L. As a result, it is possible to obtain the effect of applying the lubricant L only by the user simply gripping the tube holder 10 and moving the tube holder 10 along the medical tube C. FIG. 5 shows the state where the lubricant L is applied to the outer circumferential surface of the medical tube C.

Figure 6:
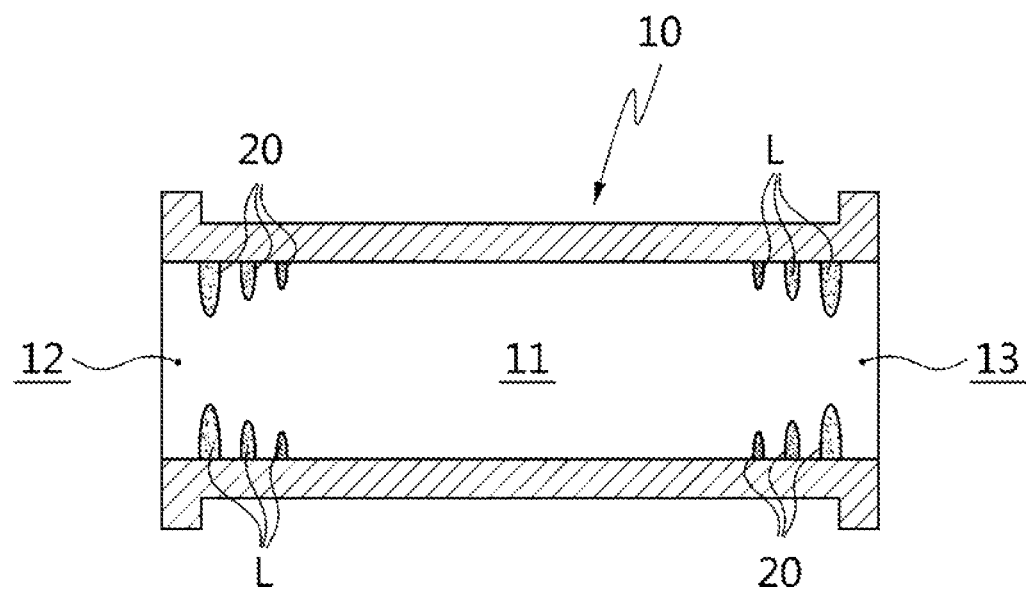
FIG. 6 is a sectional view showing an internal structure of the tube holder according to a second embodiment of the present invention.

FIG. 6 shows a second embodiment of the tube holder 10 according to the present invention. As shown in the drawing, the through hole 11 of the tube holder 10 is provided with the protruding member 20, wherein the protruding member 20 may be provided at a part of the through hole 11. For example, the protruding member 20 is provided near the inlet 12 and the outlet 13 of the through hole 11. In FIG. 6, it is exemplarily shown that three protruding members 20 are provided near the inlet 12 and the outlet 13 of the through hole 11, respectively.

Further, the protruding members 20 may have different heights along the through hole 11 of the tube holder 10. The protruding members 20 may be configured such that the height thereof is gradually decreased or increased toward the center of the through hole 11. If the height of the protruding members 20 is decreased toward the center of the through hole 11, a sufficient space is secured in the center of the through hole 11, so that the lubricant L can be more smoothly applied. On the contrary, if the height of the protruding members 20 is increased toward the center of the through hole 11, in the early stage of insertion of the medical tube C into the through hole 11 of tube holder 10, the insertion force is lowered and workability is improved.

Figure 7:
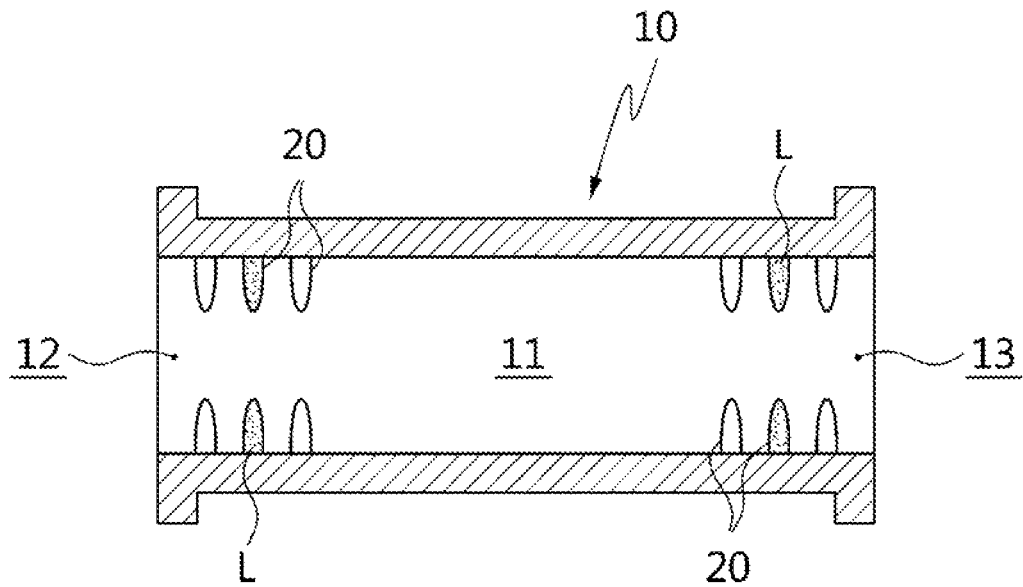
FIG. 7 is a sectional view showing an internal structure of the tube holder according to a third embodiment of the present invention.

FIG. 7 shows a third embodiment of the tube holder 10 according to the present invention. As shown in the drawing, the tube holder 10 is provided with a plurality of protruding members 20 on the inner circumferential surface thereof, wherein the protruding members 20 may be provided at a part of the through hole 11. In addition, the lubricant L may be stored in some of the plurality of protruding members 20. In FIG. 7, the lubricant L is stored only in the central protruding member 20.

As described above, if the lubricant L is stored in some of the plurality of protruding members 20, the outer protruding member 20 serves as a protection means to prevent the lubricant L from being undesirably discharged to the outside.

Figure 8:
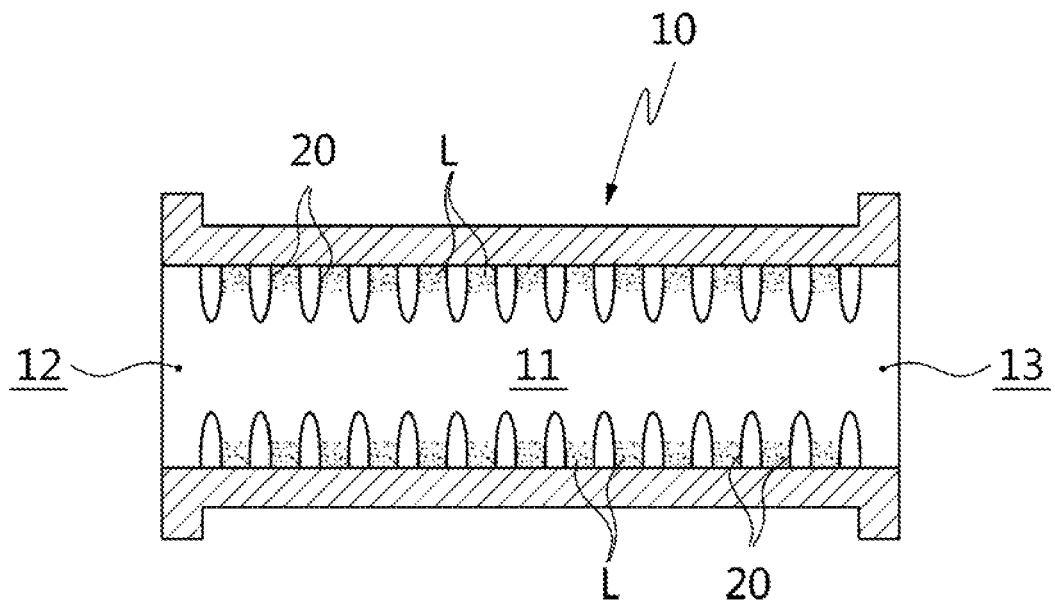
FIG. 8 is a sectional view showing an internal structure of the tube holder according to a fourth embodiment of the present invention.

Meanwhile, FIG. 8 shows a fourth embodiment of the tube holder 10 according to the present invention. As shown in the drawing, the tube holder 10 is provided with a plurality of protruding members 20 on the inner circumferential surface thereof, wherein the lubricant L is stored between the protruding members 20. In other words, the lubricant L is stored not in the protruding member 20, but stored in a space between the neighboring protruding members 20.

Preferably, the lubricant L is stored at a height lower than the height of the protruding member 20 so that the lubricant L is undesirably discharged to the outside.

Figure 9:
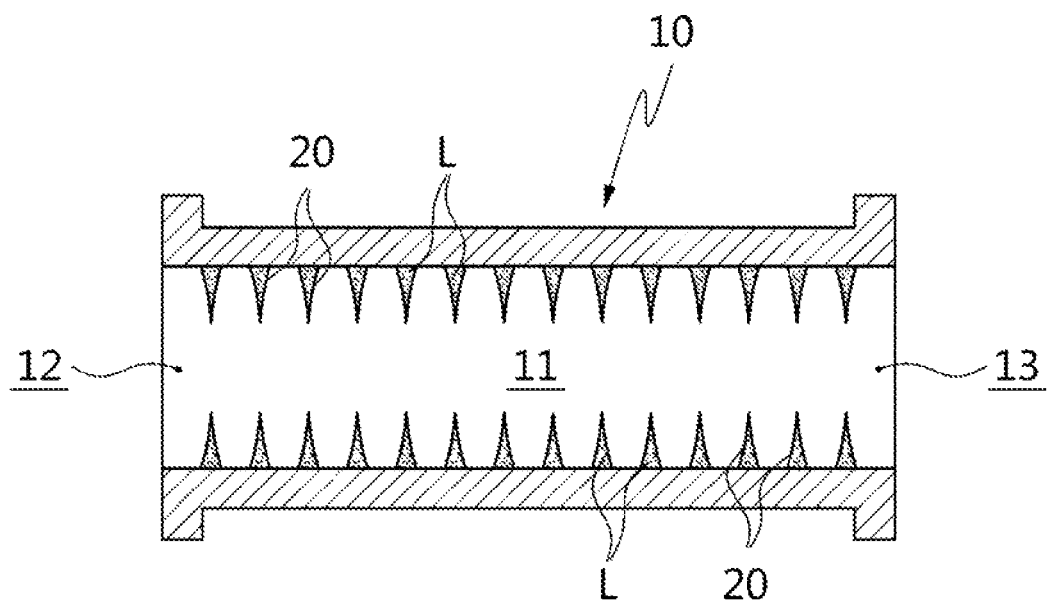
FIG. 9 is a sectional view showing an internal structure of the tube holder according to a fifth embodiment of the present invention.

FIG. 9 shows a fifth embodiment of the tube holder 10 according to the present invention. As shown in the drawing, the protrusions provided on the inner circumferential surface of the tube holder 10, which are the protruding member 20, are formed in a brush shape, the width of which narrows down toward the tip. By this structure of the protruding member 20, the protruding member 20 can be bent more gently, and thus can be easily bent and rubbed along the outer circumferential surface of the medical tube C. Also in this embodiment, the lubricant L may be stored in the protruding member 20.

Figure 10:
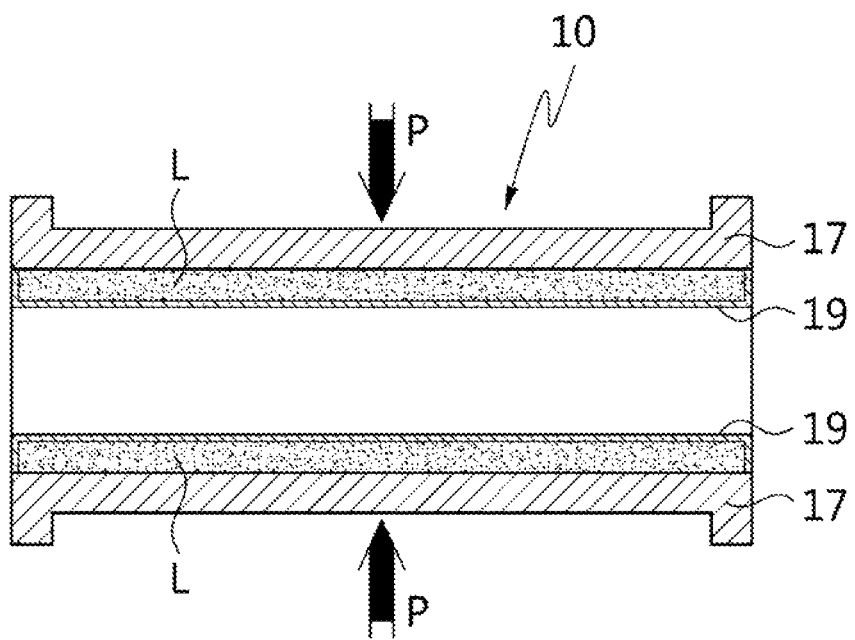
FIG. 10 is a sectional view showing an internal structure of the tube holder according to a sixth embodiment of the present invention.

FIG. 10 shows a sixth embodiment of the tube holder 10 according to the present invention. As shown in the drawing, the tube holder 10 may be provided with an inner blanket 19 therein. The inner blanket 19, which covers the inner circumferential surface of the tube holder 10, corresponds to the protruding member 20. The inner blanket 19 is made of a flexible material, wherein the lubricant L is stored in a space between the inner circumferential surface of the holder body and the inner blanket 19, and then may be applied to the outer circumferential surface of the medical tube C inserted into the through hole 11. Here, when an external force is applied in the direction of the arrow P in FIG. 10, the inner blanket 19 may be broken or torn such that the lubricant L is discharged outside. Reference numeral 17 denotes a holder body of the tube holder 10 for distinguishing from the inner blanket 19.

Figure 11:
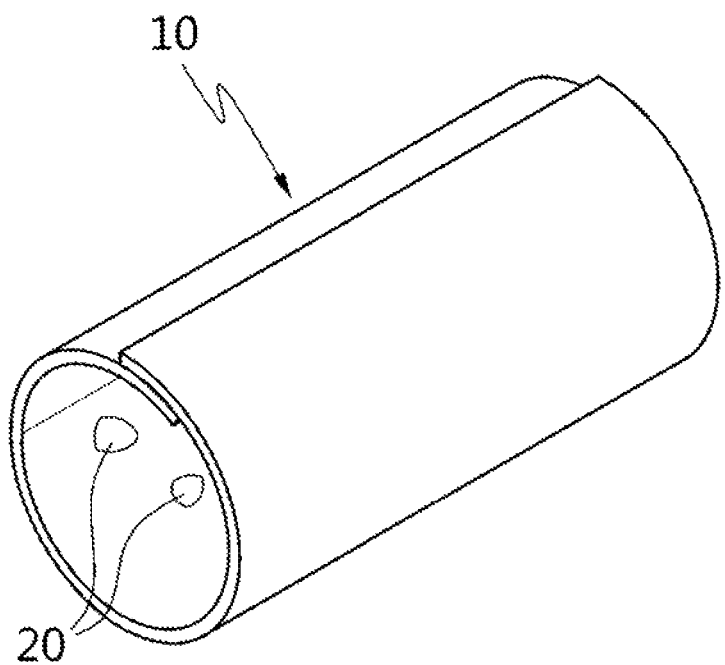
FIG. 11 is a sectional view showing an internal structure of the tube holder according to a seventh embodiment of the present invention.
Figure 12:
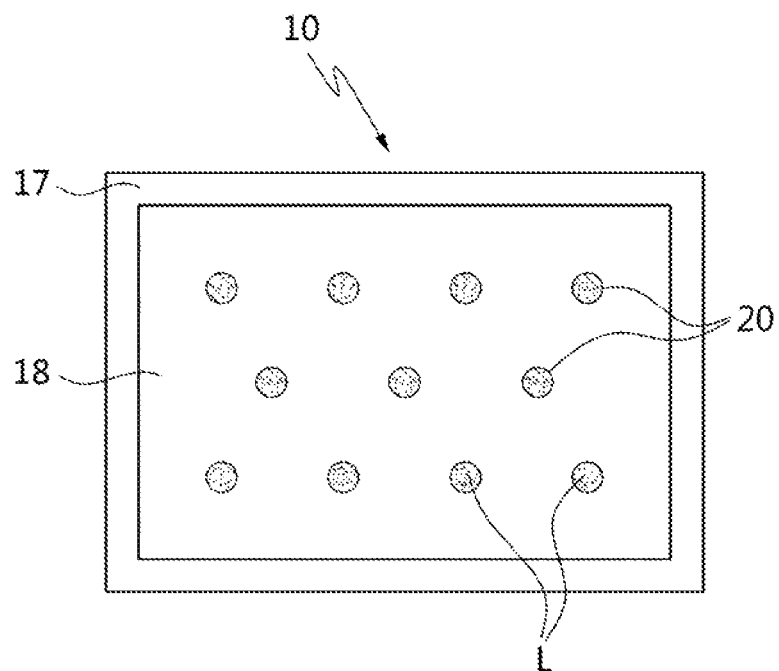
FIG. 12 is a plan view showing an unfolded state of the tube holder shown in FIG. 11.

Meanwhile, FIGS. 11 and 12 show a seventh embodiment of the tube holder 10 according to the present invention. As shown in the drawings, the holder body constituting tube holder 10 is configured such that a planar base material with opposite ends separated from each other is rolled in a cylindrical shape having the through hole 11 therein. Further, the holder body is covered with an inner blanket 18 on an inner surface thereof, and the inner blanket 18 is provided with a plurality of pockets 20 in which the lubricant L is stored.

As described above, when the tube holder 10 is bent and rolled in a cylindrical shape, with the tube holder 10 unfolded, the tube holder 10 can wrap around the outer surface of the medical tube C, and thus the tube holder 10 can be applied to the medical tube C having a different thickness.

Although not shown, instead of the inner blanket 18, the tube holder 10 may be configured such that the lubricant L is applied directly to the inner circumferential surface of the tube holder 10, or the lubricant L is stored in the protruding member 20 integrally provided with the tube holder 10.

Figure 13:
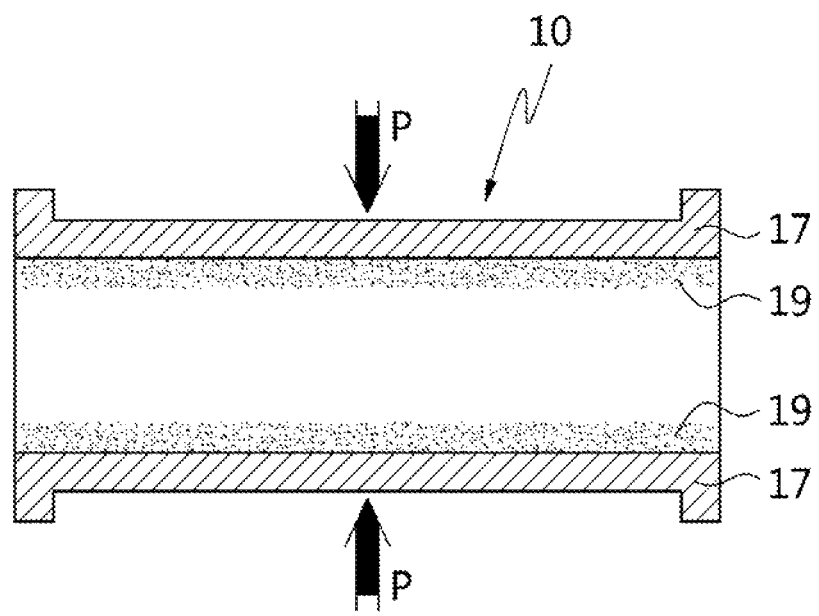
FIG. 13 is a sectional view showing an internal structure of the tube holder according to an eighth embodiment of the present invention.

For example, as shown in FIG. 13, the separate inner blanket may be omitted, and the lubrication portion 19 of the sponge material may constitute the protruding member. The lubrication portion 19 is a sponge material so it can contain the lubricant itself, and the lubricant can be applied to the outer surface of the medical tube C during contact with the medical tube C.

Meanwhile, although not shown in the above embodiments, the protruding member 20 may be a storage capsule inserted into the inner circumferential surface of the storage space of the holder body. The storage capsule is separate from the tube holder 10, and the lubricant L is stored inside the storage capsule. Further, when the storage capsule is broken by an external force, the lubricant L thereinside is discharged outside.

Here, the storage capsule may be inserted into an enlarged portion at the inlet 12 of the holder body enlarged in a direction of widening a diameter of the through hole 11.

Figure 14:
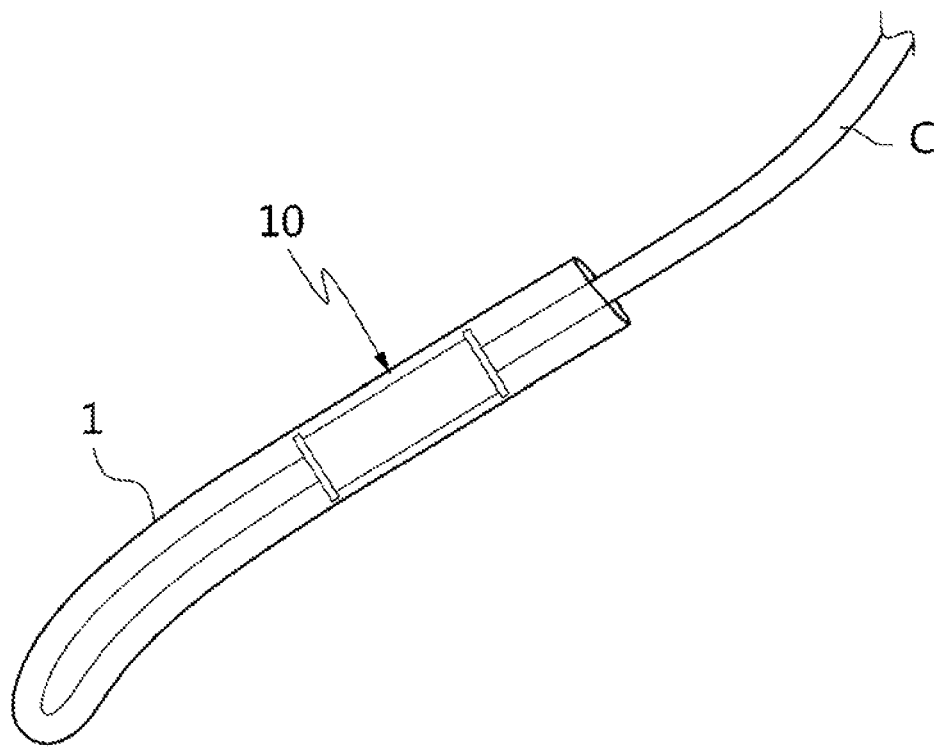
FIG. 14 is a perspective view showing a configuration of the tube holder according to a ninth embodiment of the present invention.

As shown in FIG. 14, the tube holder 10 may further include an outer protective cover 1 configured to envelop at least a part of the medical tube C including the tube holder. The outer protective cover 1 is made of vinyl material to prevent the lubricant L from escaping from the inside of the tube holder 10 during storage or transport. Further, by making the more sterilized condition through the outer protective cover 1, the hygienic use of the medical tube C is possible even when the tube holder 10 is removed.

Figure 15:
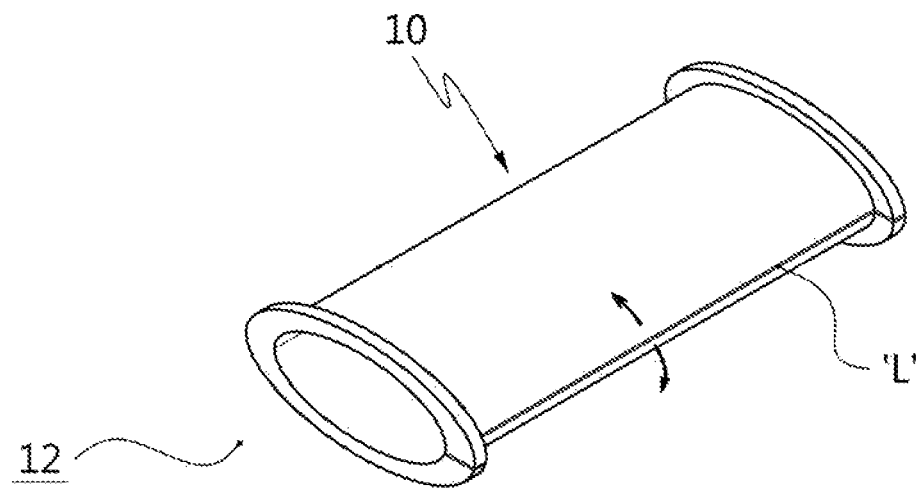
FIG. 15 is a perspective view showing a configuration of the tube holder according to a tenth embodiment of the present invention.

Further, as shown in FIG. 15, the tube holder 10 may be provided with a slit L such that one side thereof is open. The tube holder 10 is widened toward opposite sides based on the slit L (see arrow direction), so that the tube holder 10 can cover the medical tube C more easily. Further, since the tube holder 10 has a structure that can be opened at one side, the lubricant may be filled inside the tube holder 10 through the open portion. The cross-section of the tube holder 10 need not necessarily be circular, but may be an ellipse or other various shapes having voids therein, as shown in FIG. 15.

In the embodiment shown in FIG. 15, the contact means may not be the protruding member 20 but may be the left and right sides narrowing the width of the through hole 11. Of the through hole 11, when the medical tube C is inserted toward the left and right sides narrowing the width, the frictional force against the inner circumferential surface of the through hole 11 is increased, so that the tube holder can be fitted over the medical tube C.

Next, description will be made to the process of using the tube holder according to the present invention.

The tube holder 10 is fitted over the outer circumferential surface of the medical tube C, so that the user can manipulate the medical tube C by gripping the holder 10 without directly touching the medical tube C.

When the tube holder 10 is fitted over the medical tube C, the protruding member 20 provided in the tube holder 10 presses the outer circumferential surface of the medical tube C. Thereby, the tube holder 10 is prevented from being undesirably moved along the medical tube C. Further, the tube holder 10 can be applied to a medical tube C of various thicknesses even if the diameter of the through hole 11 of the tube holder 10 is somewhat large since the protruding member 20 may be rubbed against the medical tube C.

When the tube holder 10 is pressed with the tube holder 10 fitted over the medical tube C, the protruding member 20 is broken and the lubricant L stored in the protruding member 20 is discharged to be applied to the outer surface of the medical tube C. In this state, when the tube holder 10 is moved along the outer surface of the medical tube C, the protruding member 20 serves as a brush to evenly apply the lubricant L.

Of course, the protruding member 20 may be configured to be naturally broken or torn during the insertion of the medical tube C even if the tube holder 10 is not pressed. When the tube holder 10 is fitted over the medical tube C, the protruding member 20 provided in the tube holder 10 presses the outer circumferential surface of the medical tube C. Thereby, the tube holder 10 is prevented from being undesirably moved along the medical tube C. Further, the tube holder 10 can be applied to a medical tube C of various thicknesses even if the diameter of the through hole 11 of the tube holder 10 is somewhat large since the protruding member 20 may be rubbed against the medical tube C.

When the tube holder 10 is pressed with the tube holder 10 fitted over the medical tube C, the protruding member 20 is broken and the lubricant L stored in the protruding member 20 is discharged to be applied to the outer surface of the medical tube C. in this state, when the tube holder 10 is moved along the outer surface of the medical tube C, the protruding member 20 serves as a brush to evenly apply the lubricant L.

Of course, the protruding member 20 may be configured to be naturally broken or torn during the insertion of the medical tube C even if the tube holder 10 is not pressed.

As described above, the lubricant L is stored in the tube holder 10 of the present invention, and the stored lubricant L can be applied to the outer circumferential surface of the medical tube C in the process of using the tube holder 10. Thus, the user can easily apply the lubricant L using the tube holder 10, and additional work for applying the lubricant L is not required.

It should be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items. It should be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof. Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Although a preferred embodiment of the present invention has been described for illustrative purposes, those skilled in the art will appreciate that various modifications, additions and substitutions are possible, without departing from the scope and spirit of the invention as disclosed in the accompanying claims. Thus, the embodiment is therefore illustrative and not restrictive, since the scope of the invention is defined by the appended claims rather than by the description preceding them, and all changes that fall within meets and bounds of the claims, or equivalence of such meets and bounds are therefore intended to be embraced by the claims.

The invention claimed is:

1. A medical tube holder comprising:
   a holder body having a through hole therein through which a medical tube is passed; and
   a contact means provided in the holder body in a direction of narrowing a width of the through hole to increase a frictional force with an outer circumferential surface of the medical tube,
   wherein the contact means is brought into close contact with the outer circumferential surface of the medical tube passed through the through hole, such that the holder body is fitted over the medical tube,
   wherein a lubricant is provided in at least one of an inner circumferential surface of the through hole of the holder body, an inside of the contact means, and a gap between the contact means and another contact means, such that the lubricant is applied to the outer circumferential surface of the medical tube enveloped in the holder body.

2. The medical tube holder of claim 1, wherein the contact means is an elastically deformable protruding member protruding from an inner circumferential surface of the through hole of the holder body in direction of narrowing the through hole.

3. The medical tube holder of claim 2, wherein the protruding member is a plurality of protrusions having storage spaces therein configured to protrude from the inner circumferential surface of the through hole of the holder body, and
   the lubricant is stored in the protrusions or between two neighboring protrusions.

4. The medical tube holder of claim 3, wherein the protrusions are configured such that heights thereof are increased or decreased in a direction from an inlet of the through hole toward a center thereof.

5. The medical tube holder of claim 4, wherein the protrusions are made of flexible material to be bent in a direction of being brought into contact with the outer circumferential surface of the medical tube in a process of inserting the medical tube into the through hole, and
   the protrusions are broken by a force to insert the medical tube or an external force to press the protrusions, such that the lubricant stored in the storage spaces is discharged outside.

6. The medical tube holder of claim 3, wherein the protruding member is constituted by the plurality of protrusions, and
   the lubricant is stored in storage spaces of a part of the plurality of protrusions.

7. The medical tube holder of claim 2, wherein the protruding member is an inner blanket covering the inner circumferential surface of the holder body,
   the inner blanket is made of flexible material, and
   lubricant is stored in a space between the inner circumferential surface of the holder body and the inner blanket and then is applied to the outer circumferential surface of the medical tube inserted into the through hole.

8. The medical tube holder of claim 2, wherein the protruding member is a storage capsule inserted into the inner circumferential surface of a storage space of the holder body,
   the lubricant is stored in the storage capsule, and
   the storage capsule is broken by an external force and the lubricant stored therein is discharged.

9. The medical tube holder of claim 8, wherein the storage capsule is inserted into an enlarged portion at an inlet enlarged in a direction of widening a diameter of the through hole of the holder body.

10. The medical tube holder of claim 2, wherein the holder body is configured such that a planar base material with opposite ends separated from each other is rolled in a cylindrical shape having the through hole therein,
    the holder body is covered with an inner blanket on an inner surface thereof, and
    the lubricant is stored in the inner blanket.

11. The medical tube holder of claim 2, wherein the protruding member is made of sponge material, and
    lubricant is stored in the protruding member.

12. The medical tube holder of claim 1 further comprising:
    an outer protective cover configured to envelop at least a part of the medical tube including the holder body.

* * * * *